(12) United States Patent
Darouiche (10) Patent No.: US 6,475,434 B1
(45) Date of Patent: Nov. 5, 2002

(54) COMPOSITION AND METHODS FOR PREVENTING AND REMOVING BIOFILM EMBEDDED MICROORGANISMS FROM THE SURFACE OF MEDICAL DEVICES

(75) Inventor: Rabih O. Darouiche, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 09/455,985

(22) Filed: Dec. 6, 1999

Related U.S. Application Data (60) Provisional application No. 60/111,209, filed on Dec. 7, 1998.

(51) Int. Cl.[7] .............................. A61L 2/00; A61L 9/00; A01N 1/00
(52) U.S. Cl. .............................. 422/28; 422/35; 427/2.1
(58) Field of Search .............................. 422/8, 28, 35; 427/2.1

(56) References Cited

U.S. PATENT DOCUMENTS

| | | |
|---|---|---|
| 3,749,770 A | 7/1973 | Martin |
| 3,947,589 A | 3/1976 | Misato et al. |
| 4,305,958 A | 12/1981 | Fujita et al. |
| 4,710,313 A | 12/1987 | Miyajima et al. |
| 4,994,390 A | 2/1991 | Wiatr |
| 5,158,684 A | 10/1992 | Moulton et al. |
| 5,217,493 A * | 6/1993 | Raad et al. .................... 623/11 |
| 5,238,843 A | 8/1993 | Carpenter et al. |
| 5,338,480 A * | 8/1994 | Dziabo et al. ......... 252/187.21 |
| 5,419,908 A | 5/1995 | Richter et al. |
| 5,470,307 A | 11/1995 | Lindall |
| 5,480,574 A | 1/1996 | Singerman |
| 5,520,746 A | 5/1996 | Kamiya |
| 5,536,258 A | 7/1996 | Folden |
| 5,624,704 A * | 4/1997 | Darouiche et al. ......... 427/2.24 |
| 5,658,464 A | 8/1997 | Hann et al. |
| 5,658,915 A | 8/1997 | Abe et al. |

(List continued on next page.)

FOREIGN PATENT DOCUMENTS

| | | | |
|---|---|---|---|
| WO | WO 91/07090 | | 5/1991 |
| WO | WO98/07883 | * | 2/1998 |

OTHER PUBLICATIONS

Nickel et al, Tobramycin Resistance of Pseudomas aeruginosa Cells Growing as a Biofilm on Urinary Catheter Material, Apr. 1985, Antimicrobial Agents and Chemotherapy, vol. 27, No. 4, pp. 619–624.*

(List continued on next page.)

Primary Examiner—Robert J. Warden, Sr.
Assistant Examiner—Imad Soubra
(74) Attorney, Agent, or Firm—Anthony F. Matheny; Andrews & Kurth L.L.P.

(57) ABSTRACT

A biofilm penetrating composition for coating medical devices for substantially preventing the growth or proliferation of biofilm embedded microorganisms on at least one surface of the medical device is disclosed. A biofilm penetrating composition solution for cleaning medical devices which is capable of substantially removing all of the biofilm embedded microorganisms from at least one surface of medical devices is also disclosed. The biofilm penetrating composition coating and solution include a biofilm penetrating agent and may also include a base material. Medical devices coated with the biofilm penetrating composition and methods for coating medical devices and methods for removing biofilm embedded microorganisms from at least one surface of the medical devices are also disclosed.

15 Claims, 1 Drawing Sheet

U.S. PATENT DOCUMENTS

| | | | |
|---|---|---|---|
| 5,683,724 A | | 11/1997 | Hei et al. |
| 5,686,402 A | | 11/1997 | Gutierrez et al. |
| 5,691,380 A | | 11/1997 | Mason et al. |
| 5,696,164 A | | 12/1997 | Sun et al. |
| 5,719,110 A | | 2/1998 | Cook |
| 5,776,875 A | | 7/1998 | Tang et al. |
| 5,902,283 A | * | 5/1999 | Darouiche et al. ......... 604/265 |
| 6,162,487 A | * | 12/2000 | Darouiche et al. ......... 427/2.14 |

OTHER PUBLICATIONS

L. F. Prescott, R. N. Illingworth, J.A.J.H. Critchley, M.J. Stewart , R. D. Adam and A. T. Proudfoot; Intravenous N–acetycysteine: the treatment of choice for paracetamol poisoning; *British Medical Journal*, pp. 1097–1100, vol. 2; Nov. 3, 1979.

A. Gillissen, M. Jaworska, M. Orth, M. Coffiner, G. Schultze–Werninghaus, P. Maes, E.M. App, and A.M. Cantin, Nacystelyn, a novel lysine salt of N–acetylcysteine, to augment cellular antioxidant defence in vitro; *Respiratory Medicine*(1997) vol. 91, pp. 159–168.

J. C. Nickel, and I. Ruseska, J.B. Wright, and J. W. Costerton; Tobramycin Resistance of *Pseudomonas aeruginosa* Cells Growing as a Biofilm on Urinary Catheter Material; *Antimicrobial Agents and Chemotherapy*, Apr. 1985, pp. 619–624.

International Search Report, Mary 2, 2000.

Perez–Giraldo, et al., Influence of N–Acetylcysteine on the formation of biofilm by *Staphylococcus epidermis*, Journal of Antimicrobial Chemotheraphy, 1997, vol. 39, pp. 643–646.

Schierholz, et al., Investigation of rifampin, fusidic acid and mupirocin releasing silicone catheter, Biomaterials, 1998, vol. 19, pp. 2065–2074.

Ditizio, et al., A liposomal hydrogel for the prevention of bacterial adhesion to catheters, Biomaterials, 1998, vol. 19, pp. 1877–1884.

International Search Report, May 2, 2000.

Perez–Giraldo, et al., Influence of N–acetlcysteine on the formation biofilm by *Staphylococcus epidermis*, Journal of Antimicrobial Chemotherapy, 1997, vol. 39, pp. 643–646.

Schierholz, et al., Investigation of a rifampin, fusidic acid and mupirocin releasing silicone catheter, Biomaterials, 1998, vol. 19, pp. 2065–2074.

L. F. Prescott, R. N. Illingworth, J.A.J.H. Critchley, M.J. Stewart, R.D. Adam and A.T. Proudfoot; Intravenous N–acetylcysteine: the treatment of choice for paracetamol poisoning; *British Medical Journal*, pp. 1097–1100, vol. 2; Nov. 3, 1979.

J. C. Nickel, and I. Ruseska, J. B. Wright, and J. W. Costerton; Tobramycin Resistance of *Pseudomonas aeruginosa* Cells Growing as a Biofilm on Urinary Catheter Material; *Antimicrobial Agents and Chemotherapy*, Apr. 1985, pp. 619–624.

* cited by examiner

FIG.1

COMPOSITION AND METHODS FOR PREVENTING AND REMOVING BIOFILM EMBEDDED MICROORGANISMS FROM THE SURFACE OF MEDICAL DEVICES

RELATED APPLICATIONS

This application claims the benefit of U.S. Provisional Application No. 60/111,209, filed Dec. 7, 1998.

BACKGROUND OF THE INVENTION

1. Field of the Invention

The present invention relates to a composition for coating or cleaning medical devices that are likely to become contaminated or have become contaminated with microorganisms and methods for preventing biofilm embedded microorganisms from growing, or proliferating, on the surface of medical devices, and for removing biofilm embedded microorganisms growing, or proliferating, on the surface of medical devices.

2. Description of Related Art

As a defense to antimicrobial agents and other environmental hazards which may affect the survival and proliferation of microorganisms, microorganisms form a defense layer called biofilm. Formation of biofilm on the surface of various medical devices can be detrimental to the integrity of the medical device, present health risks, and prevent sufficient flow through the lumens of medical devices.

Although coating or cleaning medical devices with antimicrobial agents, e.g., antibiotics or antiseptics, can be effective in killing or inhibiting growth of planktonic organisms on the surfaces of such items, the antimicrobial agents are generally much less active against the microorganisms that are deeply embedded within the biofilm. The failure of the antimicrobial agents to sufficiently remove the microorganisms is in part due to the shielding effect of the biofilm. The biofilm prevents penetration of the antimicrobial agents deep into the biofilm to kill the microorganisms residing therein.

Accordingly, prior to the development of the present invention, there has been no biofilm penetrating composition, method for coating medical devices, method for removing biofilm embedded microorganisms from at least one surface of medical devices, or coated medical device, which: provides disruption of the biofilm thereby allowing antimicrobial agents and/or antifungal agents to penetrate the biofilm and remove biofilm embedded microorganisms from the surface of medical devices; and prevents the growth or proliferation of biofilm embedded microorganisms on the surface of medical devices. Therefore, the art has sought a biofilm penetrating composition, method for coating medical devices, method for removing biofilm embedded microorganisms from at least one surface of medical devices, or coated medical device, which: provides disruption of the biofilm thereby allowing antimicrobial agents and/or antifungal agents to penetrate the biofilm and remove biofilm embedded microorganisms from the surface of medical devices; and prevents the growth or proliferation of biofilm embedded microorganisms on the surface of medical devices. It is believed that the present invention will achieve these objectives and overcome the disadvantages of other medical devices and techniques in the field of the invention, but its results or effects are still dependent upon the skill and training of the operator.

SUMMARY OF INVENTION

In accordance with the invention the foregoing advantages have been achieved through the present composition for substantially preventing the growth or proliferation of biofilm embedded microorganisms on at least one surface of a medical device comprising at least one biofilm penetrating agent.

A further feature of the composition is that the composition may further comprise a base material. Another feature of the composition is that the at least one biofilm penetrating agent may be selected from the group consisting of cysteine and derivatives thereof. An additional feature of the composition is that the at least one biofilm penetrating agent may be selected from the group consisting of N-acetylcysteine and derivatives thereof. A further feature of the composition is that the base material may be selected from the group consisting of rubbers, thermoplastics, and elastomers. Another feature of the composition is that the base material may be selected from the group consisting of water and buffer solutions.

In accordance with the invention the foregoing advantages have also been achieved through the present composition for removing substantially all of the biofilm embedded microorganisms from at least one surface of a medical device comprising at least one biofilm penetrating agent.

A further feature of the composition is that the composition may further comprise a base material. Another feature of the composition is that the at least one biofilm penetrating agent may be selected from the group consisting of cysteine and derivatives thereof. An additional feature of the composition is that the at least one biofilm penetrating agent may be selected from the group consisting of N-acetylcysteine and derivatives thereof. A further feature of the composition is that the base material may be a buffer solution. Another feature of the composition is that the buffer solution may be phosphate buffered saline.

In accordance with the invention the foregoing advantages have also been achieved through the present method for substantially preventing the growth or proliferation of biofilm embedded microorganisms on at least one surface of a medical device comprising the steps of: providing a medical device having at least one surface; providing a biofilm penetrating composition; and contacting the biofilm penetrating composition to the medical device in an amount sufficient to substantially prevent the growth or proliferation of biofilm embedded microorganisms on the at least one surface of the medical device.

A further feature of the method for substantially preventing the growth or proliferation of biofilm embedded microorganisms on at least one surface of a medical device is that the biofilm penetrating composition may be formed by mixing cysteine or derivatives thereof and a base material. An additional feature of the method for substantially preventing the growth or proliferation of biofilm embedded microorganisms on at least one surface of a medical device is that the biofilm penetrating composition may be contacted to the medical device for a period of time sufficient to form a coating of the biofilm penetrating composition on the at least one surface of the medical device. Another feature of the method for substantially preventing the growth or proliferation of biofilm embedded microorganisms on at least one surface of a medical device is that the biofilm penetrating composition may be contacted to the medical device by integrating the biofilm penetrating composition with the material forming the medical device during formation of the medical device. A further feature of the method for substantially preventing the growth or proliferation of biofilm embedded microorganisms on at least one surface of a medical device is that the biofilm penetrating composition may be contacted to the medical device by flushing the medical device in the biofilm penetrating composition for a period of time sufficient for preventing the growth or proliferation of biofilm embedded microorganisms on at least one surface of the medical device.

In accordance with the invention the foregoing advantages also have been achieved through the present coated medical device having at least one surface which may substantially prevent the growth or proliferation of biofilm embedded microorganisms on the at least one surface of the coated medical device, comprising: (a) a medical device; and (b) a biofilm penetrating composition coating for substantially preventing the growth or proliferation of biofilm embedded microorganisms on the at least one surface of the coated medical device, the biofilm penetrating composition coating being disposed upon the at least one surface.

A further feature of the coated medical device is that the biofilm penetrating composition coating may include at least one biofilm penetrating agent. An additional feature of the coated medical device is that the biofilm penetrating composition coating may further include a base A material. Another feature of the coated medical device is that the at least one biofilm penetrating agent may be selected from the group consisting of cysteine and derivatives thereof. A further feature of the coated medical device is that the at least one biofilm penetrating agent may be selected from the group consisting of N-acetylcysteine and derivatives thereof. An additional feature of the coated medical device is that the base material may be a buffer solution.

In accordance with the invention the foregoing advantages have also been achieved through the present method for removing substantially all of the biofilm embedded microorganisms from a medical device having at least one surface, the at least one surface of the medical device having biofilm embedded microorganisms attached thereto, comprising the steps of: providing a medical device having at least one surface, the at least one surface of the medical device having biofilm embedded microorganisms attached thereto; providing a biofilm penetrating composition; and contacting the biofilm penetrating composition to the medical device in an amount sufficient to remove substantially all of the biofilm embedded microorganisms from the at least one surface of the medical device.

A further feature of the method for removing substantially all of the biofilm embedded microorganisms from a medical device having at least one surface is that the biofilm penetrating composition may be formed by mixing a biofilm penetrating agent and a base material. An additional feature of the method for removing substantially all of the biofilm embedded microorganisms from a medical device having at least one surface is that the biofilm penetrating agent may be selected from the group consisting cysteine and derivatives thereof. Another feature of the method for removing substantially all of the biofilm embedded microorganisms from a medical device having at least one surface is that the biofilm penetrating agent is selected from the group consisting of N-acetylcysteine and derivatives thereof. An additional feature of the method for removing substantially all of the biofilm embedded microorganisms from a medical device having at least one surface is that the base material is a buffer solution. A further feature of the method for removing substantially all of the biofilm embedded microorganisms from a medical device having at least one surface is that the biofilm penetrating composition may be contacted to the medical device by flushing the medical device in the biofilm penetrating composition for a period of time sufficient to substantially prevent the growth or proliferation of biofilm embedded microorganisms on the at least one surface of the medical device.

The biofilm penetrating composition, method for coating medical devices, method for removing substantially all biofilm embedded microorganisms from at least one surface of medical devices, and coated medical device of the present invention, when compared with previously proposed biofilm penetrating compositions, methods of coating medical devices, methods of removing substantially all biofilm embedded microorganisms from at least one surface of medical devices, or coated medical devices have the advantages of: providing disruption of the biofilm thereby allowing antimicrobial agents and/or antifungal agents to penetrate the biofilm and remove biofilm embedded microorganisms from the surface of medical devices; and preventing the growth or proliferation of biofilm embedded microorganisms from the surface of medical devices. It is believed that the present invention will achieve these objectives and overcome the disadvantages of other medical devices and techniques in the field of the invention, but its results or effects are still dependent upon the skill and training of the operator.

While the invention will be described in connection with the preferred embodiments, it will be understood that it is not intended to limit the invention to these embodiments. On the contrary, it is intended to cover all alternatives, modifications, and equivalents, as may be included within the spirit and scope of the invention as defined by the appended claims and equivalents thereof.

DETAILED DESCRIPTION AND SPECIFIC EMBODIMENTS

In one aspect, the present invention is directed to a biofilm penetrating composition which may be in the form of a coating which is applied to medical devices and which substantially prevents biofilm embedded microorganisms from growing and proliferating on at least one surface of the medical devices and/or substantially facilitates access of antimicrobial agents to the biofilm embedded microorganisms to assist in the prevention of the biofilm embedded microorganisms from growing or proliferating on the at least one surface of the medical device. The biofilm penetrating composition may also be in the form of a liquid, or solution, which is used to clean medical devices which include biofilm embedded microorganisms living and proliferating on at least one surface of the medical devices by flushing, rinsing, soaking, and/or any other cleaning method known to persons skilled in the art, the medical device in the biofilm penetrating composition solution, and thus, remove the biofilm embedded microorganisms from at least one surface of the medical device.

Broadly, the biofilm penetrating composition includes a biofilm penetrating agent which, in its activated state, disrupts the biofilm of microorganisms and attacks the microorganisms and/or allows other antimicrobial agents, e.g., antiseptics or antibiotics, or antifungal agents present in the biofilm penetrating composition to remove the biofilm embedded microorganisms from at least one surface of the medical devices; and/or prevents the growth or proliferation of biofilm embedded microorganisms on at least one surface of the medical device. Specifically, the biofilm penetrating composition coating for medical devices may be formulated to substantially prevent the proliferation of biofilm embedded microorganisms, and/or remove substantially all of the microorganisms, on the surface of medical devices. "Biofilm embedded microorganisms" is herein defined as any microorganism which forms a biofilm during colonization and proliferation on the surface of medical devices, including, but not limited to, gram-positive bacteria (such as *Staphylococcus epidermidis*), gram-negative bacteria (such as *Pseudomonas aeruginosa*), and/or fungi (such as *Candida albicans*). While the biofilm penetrating coating may include a biofilm penetrating agent alone, preferably, the biofilm penetrating composition coating includes a base material and a biofilm penetrating agent. The biofilm penetrating composition may also include more than one biofilm penetrating agent as desired or necessary to prevent or remove microorganisms from at least one surface of a medical device.

"Medical devices" are herein defined as disposable or permanent catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings, such as intravenous tubes, breathing tubes, dental water lines, dental drain tubes, and feeding tubes, fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field. "Medical devices" also include any device which may be inserted or implanted into a human being or other animal, or placed at the insertion or implantation site such as the skin near the insertion or implantation site, and which include at least one surface which is susceptible to colonization by biofilm embedded microorganisms. Medical devices also include any other surface which may be desired or necessary to prevent biofilm embedded microorganisms from growing or proliferating on at least one surface of the medical device, or to remove or clean biofilm embedded microorganisms from the at least one surface of the medical device, such as the surfaces of equipment in operating rooms, emergency rooms, hospital rooms, clinics, and bathrooms. In one specific embodiment, the biofilm penetrating composition is integrated into an adhesive, such as tape, thereby providing an adhesive which may prevent growth or proliferation of biofilm embedded microorganisms on at least one surface of the adhesive.

Implantable medical devices include orthopedic implants which may be inspected for contamination or infection by biofilm embedded microorganisms using endoscopy. Insertable medical devices include catheters and shunts which can be inspected without invasive techniques such as endoscopy. The medical devices may be formed of any suitable metallic materials or non-metallic materials known to persons skilled in the art. Examples of metallic materials include, but are not limited to, tivanium, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex (polytetrafluoroethylene), Dacron® (polyethylene tetraphthalate), Teflon (polytetrafluoroethylene), latex, elastomers and Dacron® sealed with gelatin, collagen or albumin, and derivatives or combinations thereof. The medical devices include at least one surface for applying the biofilm penetrating composition. Preferably, the biofilm penetrating composition is applied to the entire medical device.

The biofilm penetrating composition may include any number of biofilm penetrating agents and base materials known to persons skilled in the art. Preferably, the biofilm penetrating agents have mucolytic capabilities, i.e., the ability to break-up and penetrate mucous, and/or the capability of penetrating and breaking-up microorganism biofilm.

Suitable biofilm penetrating agents include the amino acid cysteine and cysteine derivatives. Examples of suitable biofilm penetrating agents include cysteine (L-cysteine, D-cysteine, DL-cysteine), DL-Homocysteine, L-cysteine methyl ester, L-cysteine ethyl ester, N-carbamoyl cysteine, cysteamine, N-(2-mercaptoisobutyryl)-L-cysteine, N-(2-mercaptopropionyl)-L-cysteine-A, N-(2-mercaptopropionyl)-L-cysteine-B, N-(3-mercaptopropionyl)-L-cysteine, L-cysteine ethyl ester hydrochloride, L-cysteine methyl ester hydrochloride, nacystelyn (a lysine salt of N-acetylcysteine), N-acetylcysteine, and derivatives thereof. Preferably, the biofilm penetrating agent is N-acetylcysteine and derivatives thereof.

N-acetylcysteine corresponds to the chemical formula $C_5 H_9 NO_3 S$ and the following chemical structure:

N-acetylcysteine is an "acetylated" derivative of the amino acid cysteine. Cysteine, and all amino acids more complex than glycine, exists as two enantiomeric forms, the naturally occurring "L" form and its non-naturally occurring "D" form. The "L" form of N-acetylcysteine, which is designated N-acetyl-L-cysteine, is preferred for use herein, because it is more readily available, although the "D" form can be used. It is also recognized that cysteine and its N-acetylated derivative can exist as an oxidized dimer, however, the monomeric form of N-acetylcysteine is preferred for use herein.

While N-acetyl-L-cysteine is preferred, it is contemplated that derivatives of N-acetylcysteine may also be used as biofilm penetrating agent. These derivatives include esters, amides, anhydrides, and thio-esters and thio-ethers of the sulfhydryl moiety. Examples of suitable N-acetylcysteine derivatives include, but are not limited to, methyl-N-acetylcysteine, ethyl N-acetylcysteine, stearyl N-acetylcysteine, N-acetylcysteine methylthioether, N,S-diacetylcysteine, N-acetylcysteine amide, N-mercaptoacetyl-L-cysteine, and the mixed anhydride of N-acetylcysteine and acetic acid.

It is also contemplated that pharmaceutically acceptable salts of N-acetylcysteine and derivatives of N-acetylcysteine may also be used as biofilm penetrating agents. Non-limiting examples of these salts include sodium salts, e.g., N-acetyl-L-cysteine sodium salt and N-acetyl-L-cysteine sodium zinc monohydrate, potassium salts, magnesium salts, e.g., N-acetyl-L-cysteine magnesium zinc salts, calcium salts, e.g., N-acetyl-L-cysteine calcium zinc monohydrate, zinc salts, e.g., N-acetyl-L-cysteine zinc salt, zinc mercaptide salts, ammonium slats, e.g., N-acetyl-L-cysteine ammonium zinc salt, calcium zinc N-acetyl-L-cysteinate acetate, zinc mercaptide N-acetylcysteine carboxylates, and alkyl ammonium and alkanol ammonium salts, i.e., wherein the ammonium ion is substituted with one or more alkyl or alkanol moieties.

The biofilm penetrating agent is included in the biofilm penetrating composition in amounts sufficient to penetrate, or break-up the biofilm and provide the biofilm penetrating agent, antimicrobial agent, and/or antifungal agent access to the biofilm embedded microorganisms thereby facilitating the removal of substantially all of the biofilm embedded microorganisms from at least one surface of the medical device. While the biofilm penetrating agent may be 100% of the biofilm penetrating composition, preferably, the biofilm penetrating composition contains from at least about 0.01% to about 60% biofilm penetrating agent by weight based upon the total weight of the biofilm penetrating composition being employed. In the preferred embodiment, the biofilm penetrating composition includes from at least about 0.5% to about 30% (by weight) biofilm penetrating agent.

The term "base material" is defined herein as any of a group of materials which effectively disperses the biofilm penetrating agent at an effective concentration to penetrate, or break-up, the biofilm thereby facilitating access of the biofilm penetrating agent, antimicrobial agents, and/or antifungal agents to the microorganisms embedded in the biofilm, and thus, removal of substantially all of the microorganisms from at least one surface of the medical device. The term "base material" also includes any group of solutions which effectively disperse the biofilm penetrating agent at an effective concentration to form a biofilm penetrating composition coating for medical devices which substantially prevents the growth or proliferation of biofilm embedded microorganisms on at least one surface of the medical device. In the case of the biofilm penetrating composition coating, preferably, the base material also facilitates the adhesion of the biofilm penetrating composition to at least one surface of the medical device and prevents the biofilm penetrating composition coating from being easily removed from the surface of the medical device, thereby facilitating the utilization of the biofilm penetrating composition to coat at least one surface of a medical device.

Examples of suitable base materials include, but are not limited to, buffer solutions, phosphate buffered saline, saline, water, polyvinyl, polyethylene, polyurethane, polypropylene, silicone (e.g., silicone elastomers and silicone adhesives), polycarboxylic acids, (e.g., polyacrylic acid, polymethacrylic acid, polymaleic acid, poly-(maleic acid monoester), polyaspartic acid, polyglutamic acid, aginic acid or pectimic acid), polycarboxylic acid anhydrides (e.g., polymaleic anhydride, polymethacrylic anhydride or polyacrylic acid anhydride), polyamines, polyamine ions (e.g., polyethylene imine, polyvinylarnine, polylysine, poly-(dialkylamineoethyl methacrylate), poly-(dialkylaminomethyl styrene) or poly-(vinylpyridine)), polyammonium ions (e.g., poly-(2-methacryloxyethyl trialkyl ammonium ion), poly-(vinylbenzyl trialkyl ammonium ions), poly-(N.N.-alkylypyridinium ion) or poly-(dialkyloctamethylene ammonium ion) and polysulfonates (e.g. poly-(vinyl sulfonate) or poly-(styrene sulfonate)), collodion, nylon, rubber, plastic, polyesters, Gortex (polytetrafluoroethylene), Dacron® (polyethylene tetraphthalate), Teflon polytetrafluoroethylene), latex, and derivatives thereof, elastomers and Dacron(® sealed with gelatin, collagen or albumin, cyanoacrylates, methacrylates, papers with porous barrier films, adhesives, e.g., hot melt adhesives, solvent based adhesives, and adhesive hydrogels, fabrics, and crosslinked and non-crosslinked hydrogels, and any other polymeric materials which facilitate dispersion of the biofilm penetrating agent and adhesion of the biofilm penetrating coating to at least one surface of the medical device. Linear copolymers, cross-linked copolymers, graft polymers, and block polymers, containing monomers as constituents of the above exemplified polymers may also be used.

The term "polyvinyl" is defined herein as any of a group of polymerized vinyl compounds such as PV-coA-coA (Polyvinyl butyryl-co-vinyl alcohol-co-vinylacetate), PV-coA-coA plus hydroxylapatite, PVP (Polyvinyl pyrrolidone), PVP-co-VA (Polyvinyl pyrrolidone co-vinyl acetate dissolved in 2-propanol) and combinations thereof.

The term "nylon" is defined herein as any of a group of synthetic long-chain polymeric amides with recurring amide groups having great strength and elasticity, such as polycaprolactam, polylauryl-lactam and polyhexamethylene sebacamide.

The term "collodion" is defined herein as any of a group of colorless or pale-yellow, viscous solutions of pyroxylin or nitrocellulose in a mixture of alcohol and ether, which dries quickly and forms a tough, elastic film.

While the biofilm penetrating composition may include any number of biofilm penetrating agents and base materials, in the case of internal or external use of the biofilm penetrating composition with humans or animals, the biofilm penetrating agent and base material should be biocompatible with the human beings or animals in which the medical device is inserted or implanted. "Biocompatible" is herein defined as compatible with living tissues, such that the medical device is not rejected or does not cause harm to the living tissue.

The term "effective concentration" is herein defined as a sufficient amount of the biofilm penetrating agent to substantially prevent the growth or proliferation of biofilm embedded microorganisms on the at least one surface of the medical device in the case of the biofilm penetrating composition being a coating; and as a sufficient amount of the biofilm penetrating agent to substantially penetrate, or break-up, the biofilm on the at least one surface of the medical device, thereby facilitating access of the biofilm penetrating agent, antimicrobial agents, and/or antifungal agents to the microorganisms embedded in the biofilm, and thus, removal of substantially all of the microorganisms from at least one surface of the medical device in the case of the biofilm penetrating composition being a solution. The amount will vary for each of the biofilm penetrating agents and upon known factors such as pharmaceutical characteristics; the type of medical device; the degree of biofilm embedded microorganism contamination; and the use and length of use. It is within the ability of a person of ordinary skill in the art to relatively easily determine an effective concentration for each biofilm penetrating agent.

In one embodiment, the biofilm penetrating composition solution is formed by combining 31 mg/ml N-acetylcysteine in phosphate buffered saline at a concentration equivalent to 10 times the minimal bactericidal concentration of N-acetylcysteine for the infecting strain *Staphylococcus epidermidis*. The concentration of N-acetylcysteine, or any other biofilm penetrating agent, present in the biofilm penetrating composition, may be adjusted as desired or necessary without undue experimentation by persons skilled in the art. Preferably, antimicrobial agents and/or antifungal agents, may be included in the biofilm penetrating composition at desired or necessary concentrations.

In another aspect, the invention is directed to a method for coating a medical device. Broadly, the method for coating a medical device includes the steps of providing a medical device, providing, or forming, a biofilm penetrating composition coating, and applying the biofilm penetrating composition coating to at least one surface of the medical device in an amount sufficient to substantially prevent the growth or proliferation of biofilm embedded microorganisms on at least one surface of the medical device.

In one specific embodiment, the method for coating a medical device includes the steps of forming a biofilm penetrating composition of an effective concentration for activating the biofilm penetrating agent, and thus substantially preventing the growth or proliferation of microorganisms on at least one surface of the medical device, wherein the biofilm penetrating composition is formed by combining a biofilm penetrating agent and a base material. At least one surface of the medical device is then contacted with the biofilm penetrating composition under conditions wherein the biofilm penetrating composition covers at least one surface of the medical device. "Contacting" includes, but is not limited to, impregnating, compounding, mixing, integrating, coating, spraying and dipping.

In another aspect the invention relates to a method for removing substantially all of the biofilm embedded microorganisms from at least one surface of the medical device. In one specific embodiment, the method of removing substantially all of the biofilm embedded microorganisms from at least one surface of the medical device includes the steps of providing a medical device having at least one surface, the at least one surface having biofilm embedded microorganisms attached thereto, and contacting the medical device with a biofilm penetrating composition as described in greater detail above. "Contacting") further includes, but is not limited to, soaking, rinsing, flushing, submerging, and washing. The medical device should be contacted with the biofilm penetrating composition for a period of time sufficient to remove substantially all of the biofilm embedded microorganisms from the at least one surface of the medical device. In one specific embodiment, the medical device is submerged in the biofilm penetrating composition for at least 5 minutes. Alternatively, the medical device may be flushed with the biofilm penetrating composition. In the case of the medical device being a tubing, such as dental drain tubing, the biofilm penetrating composition may be poured into the dental drain tubing and both ends of the tubing clamped such that the biofilm penetrating composition is retained within the lumen of the tubing. The tubing is then allowed to remained filled with the biofilm penetrating composition for a period of time sufficient to remove substantially all of the biofilm embedded microorganisms from at least one surface of the medical device, generally, for at least about 1 minutes to about 48 hours. Alternatively, the dental tubing may be flushed by pouring the biofilm penetrating composition into the lumen of the dental tubing for an amount of time sufficient to prevent, or remove, substantially all biofilm embedded microorganism growth.

In this embodiment, the biofilm penetrating composition is preferably formed by combining a biofilm penetrating agent and a base material at room temperature and mixing the biofilm penetrating composition for a time sufficient to evenly disperse the biofilm penetrating agent in the biofilm penetrating composition prior to contacting the medical device to the biofilm penetrating composition. The concentration of biofilm penetrating agent in the biofilm penetrating compositions may vary as desired or necessary to decrease the amount of time the biofilm penetrating composition is in contact with the medical device. These variations in biofilm penetrating agent concentration are easily determined by persons skilled in the art.

In specific embodiments of the method for coating medical devices and the methods for removing substantially all of the biofilm embedded microorganisms from at least one surface of the medical devices, the step of forming a biofilm penetrating composition may also include any one or all of the steps of adding an organic solvent, a medical device material penetrating agent, or adding an alkalinizing agent to the biofilm penetrating composition, to enhance the reactivity of the surface of the medical device with the biofilm penetrating composition. In the case of the method for coating medical devices, the organic solvent, medical device material penetrating agent, and/or alkalinizing agent preferably facilitate adhesion of the biofilm penetrating composition to at least one surface of the medical device.

The term "organic solvent" is herein defined as solvents that can be used to dissolve microbial indicator agents, including, but not limited to, alcohols, e.g., methanol and ethanol, ketones, e.g., acetone and methylethylketone, ethers, e.g., tetrahydrofuran, aldehydes, e.g.,. formaldehyde, acetonitrile, acetic acid, methylene chloride, chloroform, carbonates, water, and alkyl hydrocarbons, e.g., hexane and heptane, and xylene, or similar solvents.

The term "medical device material penetrating agent" is herein defined as an organic compound that can be used to promote penetration of the microbial indicator agent into the surface of the medical device. Suitable penetrating agents include esters, e.g., ethyl acetate, propyl acetate, butyl acetate, amyl acetate, and combination thereof, ketones, e.g., acetone and methylethylketone, methylene chloride, chloroform, and xylene.

The term "alkalinizing agent" is herein defined as organic and inorganic bases including sodium hydroxide, potassium hydroxide, alkyl hydroxides, ammonia in water (27% ammonium hydroxide), diethylamine and triethylamine.

The term "high ionic strength salts" is herein defined as salts exhibiting high ionic strength, such as sodium chloride, potassium chloride, ammonium acetate. These salts may act both as an alkalinizing agent and as a penetrating agent to enhance the reactivity of the surface of the medical device. Therefore, in one specific embodiment, high ionic strength salts may also be used in the step of forming the biofilm penetrating composition.

In another embodiment of the method for coating a medical device, the biofilm penetrating composition coating is preferably formed by combining a biofilm penetrating agent and a base material at room temperature and mixing the biofilm penetrating composition for a time sufficient to evenly disperse the biofilm penetrating agent in the biofilm penetrating composition prior to applying the biofilm penetrating composition to a surface of the medical device. The medical device may be contacted with the biofilm penetrating composition for a period of time sufficient for the biofilm penetrating composition to adhere to at least one surface of the medical device. After the biofilm penetrating composition is applied to a surface of the medical device, it is allowed to dry.

The medical device is preferably placed in contact with the biofilm penetrating composition by dipping the medical device in the biofilm penetrating composition for a period of time ranging from about 5 seconds to about 120 minutes at a temperature ranging from about 25° C. to about 80° C. Preferably, the medical device is placed in contact with the biofilm penetrating composition by dipping the medical device in the biofilm penetrating composition for about 60 minutes at a temperature of about 45° C.

The medical device is then removed from the biofilm penetrating composition and the biofilm penetrating composition is allowed to dry. The medical device may be placed in an oven, or other heated environment for a period of time sufficient for the biofilm penetrating composition to dry. Preferably, the medical device is placed in a heated environment having a temperature of about 80° F. to about 180° F. for about 3 minutes to about 30 minutes. Preferably, the medical device is placed in an oven at a temperature ranging from about 120° F. to about 160° F for about 10 minutes to about 20 minutes.

Although one layer, or coating, of the biofilm penetrating composition is believed to provide the desired biofilm penetrating composition coating, multiple layers are preferred. The multiple layers of the biofilm penetrating composition are preferably applied to the at least one surface of the medical device by repeating the steps discussed above. Preferably, the medical device is contacted with the biofilm penetrating composition three times, allowing the biofilm penetrating composition to dry on at least one surface of the medical device prior to contacting the medical device with the biofilm penetrating composition for each subsequent layer. In other words, the medical device preferably includes three coats, or layers, of the biofilm penetrating composition on at least one surface of the medical device.

In another embodiment, the method for coating medical devices with a biofilm penetrating composition coating includes the steps of forming a biofilm penetrating composition coating of an effective concentration to substantially prevent the growth or proliferation of biofilm embedded microorganisms on at least one surface of the medical device by dissolving a biofilm penetrating agent in an organic solvent, combining a medical device material penetrating agent to the biofilm penetrating agent and organic solvent, and combining an alkalinizing agent to the biofilm penetrating agent, organic solvent, and medical device material penetrating agent to improve the reactivity of the material of the medical device. The biofilm penetrating composition is then heated to a temperature ranging from about 30° C. to about 70° C. to enhance the adherence of the biofilm penetrating composition coating to at least one surface of the medical device. The biofilm penetrating composition coating is applied to at least one surface of the medical device, preferably by contacting the biofilm penetrating composition coating to the at least one surface of the medical device for a sufficient period of time for the biofilm penetrating composition coating to adhere to at least one surface of the medical device. The medical device is removed from the biofilm penetrating composition coating and allowed to dry for at least 8 hours, and preferably, overnight, at room temperature. The medical device may then be rinsed with a liquid, such as water and allowed to dry for at least 2 hours, and preferably 4 hours, before being sterilized. To facilitate drying of the biofilm penetrating composition onto the surface of the medical device, the medical device may be placed into a heated environment such as an oven. For example, the medical device may be placed into an oven at 140° F. for fifteen minutes to facilitate drying the biofilm penetrating composition onto the surface of a medical device. Preferably, multiple layers of the biofilm penetrating composition coating is applied to the at least one surface of the medical device by repeating the steps above.

In another embodiment, the method for coating the medical devices with a biofilm penetrating composition includes the steps of forming the biofilm penetrating composition and incorporating the biofilm penetrating composition into the material forming the medical device during the formation of the medical device. For example, the biofilm penetrating composition may be combined with the material forming the medical device, e.g., silicone, polyurethane, polyethylene, Gortex (polytetrafluoroethylene), Dacron® (polyethylene tetraphthalate), Teflon® (polytetrafluoroethylene), and/or polypropylene, and extruded with the material forming the medical device, thereby incorporating the biofilm penetrating composition into material forming the medical device. In this embodiment, the biofilm penetrating composition may be incorporated in a septum or adhesive which is placed at the medical device insertion or implantation site. An example of a coated medical device having a biofilm penetrating composition incorporated into the material forming the medical device in accordance with this embodiment is the catheter insertion seal having an adhesive layer described below in greater detail.

In still another aspect, the invention is directed to coated medical devices. Broadly, the coated medical devices include a biofilm penetrating composition coating applied to at least one surface of the medical device. Suitable medical devices and biofilm penetrating compositions are described above in greater detail. The biofilm penetrating composition may be applied to at least one surface of the medical devices in any suitable manner. For example, the biofilm penetrating composition may be applied to the medical devices following any of the methods described above in greater detail.

In one specific embodiment, a septum, or adhesive layer, is made of a breathable material which has small enough porosity to allow moisture to pass, but functions as a barrier to microorganisms thereby facilitating a lower incidence of microorganism colonization and resulting contamination or infection. The adhesive layer may also include a layer of gauze to facilitate a lower incidence of microorganism colonization and resulting contamination or infection. The coated medical devices in this specific embodiment permit only limited contact of the biofilm penetrating composition with the body and/or blood, thereby decreasing the potential for allergic reactions.

Figure 1:
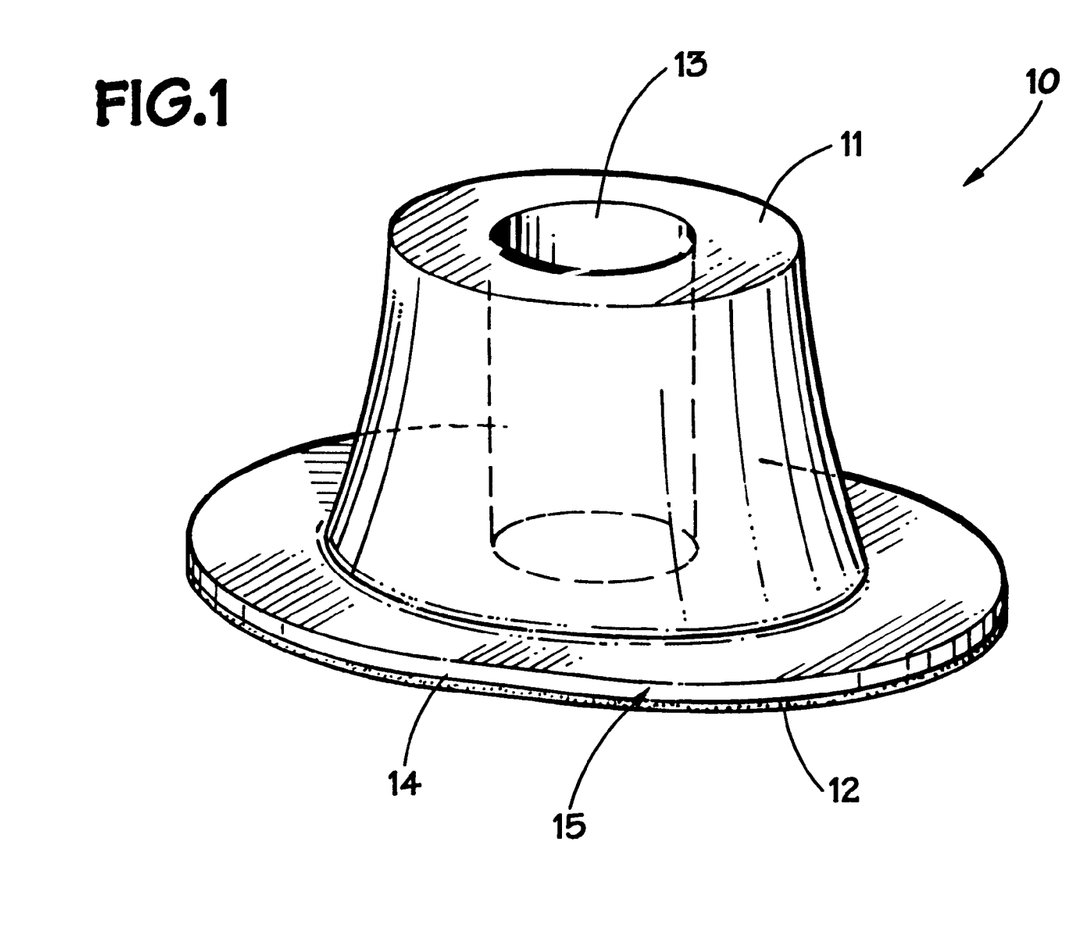
FIG. 1 is a specific embodiment of a catheter insertion seal having a biofilm penetrating composition incorporated into an adhesive layer located on the catheter insertion seal.

Referring now to FIG. 1, in one specific embodiment, the invention is directed to a catheter insertion seal 10 which includes the biofilm penetrating composition 15. In this embodiment, the catheter insertion seal 10 includes a first end 11, a second end 12, and an aperture 13 connecting first end 11 in second end 12. Aperture 13 runs through the catheter insertion seal 10, thereby connecting first end 11 and second end 12.

Second end 12 includes an adhesive layer 14 which facilitates securing the catheter insertion seal 10 to the external surface of a human being or animal, i.e., the skin. Alternatively, adhesive layer 14 may be an integral part of the catheter insertion seal 10. A catheter (not shown) may then be placed through the catheter insertion seal 10 by passing the catheter through the aperture 13. Aperture 13 may be connected to first end 11 and second end 12 at an angle (not shown) less than 90 degrees, to facilitate insertion of the catheter through the aperture 13 and into the human being or animal. The catheter may then be secured to the catheter insertion seal 10 by any method known to persons skilled in the art. For example, the catheter insertion seal 10 may include tabs (not shown) or flanges (not shown) which are reciprocal to tabs or flanges on the catheter, which, when engaged with one another, secure the catheter to the catheter insertion seal 10. A mechanical interference fit between the aperture 13 and the outer diameter of the catheter may also secure the catheter to the catheter insertion seal 10.

The adhesive layer 14 may be formed out of any material known to persons skilled in the art provided the adhesive layer 14 includes at least one side having a "sticky" adhesive for securing the catheter insertion seal 10 to the external surface of the human being or other animal. For example, adhesive layer 14 may be formed out of any of the materials identified above regarding medical devices and base material.

The biofilm penetrating composition 15 may be incorporated into the adhesive layer 14 by any method known to persons skilled in the art. For example, the biofilm penetrating composition may be incorporated into the adhesive layer 14 as discussed above in greater detail. Accordingly, the adhesive layer 14 facilitates securing the catheter insertion seal 10, and thus the catheter, to the external surface of the human being or other animal, prevents and/or removes substantially all microorganism growth or proliferation along the surface of the catheter insertion seal 10, and provides a defense from contamination or infection at the insertion or implantation site by keeping microorganisms away from the insertion or implantation site.

The following examples are offered by way of illustration and are not intended to limit the invention in any manner. For example, other biofilm penetrating compositions may be formed having lower concentrations of a biofilm penetrating agent which is capable of preventing or removing microorganisms growth along the at least one surface of the medical device. Further, other bifilm penetrating compositions may be formed at concentrations sufficient for preventing or removing microorganism growth along the at least one surface of the medical device depending on the cause of the microorganism contamination.

EXAMPLE 1

Seeding phase: A dynamic flow sterile system that consisted of an infusion bad containing a bacterial suspension of *Staphylococcus epidermidis* ($4 \times 10^5$ cfu/ml of saline) that infused at equal (about 41 ml/hour) into the lumens of eight ethylene oxide gas sterilized, 7-french, 20 cm polyurethane, single-lumen catheters for 12 hours at room temperature. The catheters were covered plastic sheath to ensure sterility of the surfaces. The bacterial suspension drained from the catheters into beakers.

Growth phase: The lumens of the four catheters were infused with sterile trypticase soy broth ("TSB") at a rate of 10 ml/hour for 24 hours to allow for biofilm formation. The infused broth drained from the catheters into the beakers.

Treatment phase: The lumens of the eight catheters were treated with biofilm penetrating composition solutions as described in Table I. The N-acetylcysteine and rifampin are used at a concentration equivalent to ten times the corresponding minimal bactericidal concentration of the N-aceylcysteine and the rifampin for the studied strain of *Staphylococcus epidermidis* (3.1 mg/ml and 0.02 μg/ml respectively).

TABLE I

| Catheter | Catheter Solution |
|---|---|
| 1 | Control (Phosphate-buffered saline) |
| 2 | Control (Phosphate-buffered saline) |
| 3 | Phosphate buffered saline + 31 mg/ml N-acetylcysteine |

TABLE I-continued

| Catheter | Catheter Solution |
|---|---|
| 4 | Phosphate buffered saline + 31 mg/ml N-acetylcysteine |
| 5 | Phosphate buffered saline + 0.2 μg/ml rifampin |
| 6 | Phosphate buffered saline + 0.2 μg/ml rifampin |
| 7 | Phosphate buffered saline + 31 mg/ml N-acetylcysteine + 0.2 μg/ml rifampin |
| 8 | Phosphate buffered saline + 31 mg/ml N-acetylcysteine + 0.2 μg/ml rifampin |

The treatment solutions in Table I were instilled into the catheter lumens, and the two ends of each catheter were clamped and the solutions were allowed to remain in the lumens of the catheters for four hours at room temperature.

After four hours the catheters were cultured by two methods. Catheters 1, 3, 5 and 7 were cultured by flushing and Catheters 2, 4, 6, and 8 were cultured by sonication.

The clamps were removed from each end of Catheters 1, 3, 5, and 7 and the treatment solutions were drained. Two milliliters of air was pushed through the lumen of each catheter using a syringe. Each catheter lumen was then flushed briskly three times with 4 ml of sterile TSB and the flushed TSB was collected in designated Erlenmeyer flasks. Hundred microliter aliquots of the collected portions of the flushed TSB and 10-fold serial dilutions were inoculated onto chocolate agar plates and colony counts were determined after incubation of agar plates at 37° C. for 48 hours. Results are in Table II.

The clamps were removed from each end of Catheters 2, 4, 6, and 8 and the treatment solutions drained. Using sterile gloves and razor blades, each catheter was placed on a sterile surface and both the proximal and distal 1 cm segments of each catheter was cut off and discarded. The remaining 18 cm portion of each catheter was cut into six, 3 cm segments, each of which was sliced down the middle to expose the lumen. Each 3 cm segment was placed in 5 ml of phosphate buffered saline and sonicated for 1 minute. Hundred microliter aliquots of the sonicated fluid and 10-fold serial dilutions were inoculated onto chocolate agar plates and allowed to incubate at 37° C. for 48 hours. Colony counts were determined after incubation of agar plates and the average number of colonies in each agar plate for each treatment solution was then determined. Results are in Table III

TABLE II

FLUSH CULTURES

| Catheter | Number of Colonies (cfu per catheter) |
|---|---|
| 1 | $3.5 \times 10^5$ |
| 3 | No growth |
| 5 | $1.1 \times 10^4$ |
| 7 | No growth |

TABLE III

SONICATION CULTURES

| Catheter | Number of Colonies (mean cfu per 3 cm catheter) |
|---|---|
| 2 | 33 |
| 4 | 0 |
| 6 | 0 |
| 8 | 8.3 |

These results show that N-acetylcysteine effectively penetrates and breaks-up the biofilm and kills biofilm embedded microorganisms such as *Staphylococcus epidermidis*. At the concentration used, the antimicrobial activity of N-acetylcysteine against biofilm embedded microorganisms when assessed by flush cultures also surpasses the antimicrobial activity of rifampin, one of the more active antibiotics against staphylococcal organisms. As shown in the above example, N-acetylcysteine may be used alone or in combination with antimicrobial agents and/or antifungal agents. For instance, the combination of N-acetylcysteine with antimicrobial agents may provide the unique advantage of penetrating the biofilm, thereby facilitating access of the antimicrobial agents and/or antifungal agents to the biofilh embedded microorganisms, thereby enhancing the ability of the antimicrobial agents and/or antifungal agents to more effectively remove biofilm embedded microorganisms from at least one surface of the medical device.

EXAMPLE 2

Seeding Phase: A dynamic flow sterile system that consisted of an infusion bag containing a bacterial suspension of *Staphylococcus epidermidis* ($10^5$ cfu/ml of saline) that infused at equal rates (about 40 ml/hour) for 12 hours at room temperature into the lumens of four gas-sterilized, 7-french, 20 cm polyurethane, single lumen catheters that were coated as described in Table IV.

TABLE IV

| Catheter | Catheter Coating Composition |
| --- | --- |
| 9 | Control uncoated catheter |
| 10 | Catheter coated with N-acetylcysteine (50 mg/ml of coating composition) |
| 11 | Catheter coated with rifampin (40 mg/ml of coating composition) |
| 12 | Catheter coated with N-acetylcysteine (50 mg/ml of coating composition) and rifampin (40 mg/ml of coating composition) |

All of the biofilm penetrating coatings applied to Catheters 10–12 were prepared as follows with the differences between the addition of either N-acetylcysteine or rifampin to the biofilm penetrating composition coating in the concentrations identified above.

The biofilm penetrating composition coatings were formed by dissolving 75 mg of sodium hydroxide in 15 ml of methanol while stirring until clear, yielding a concentration of 5 mg sodium hydroxide per ml of methanol. The dissolution was more rapidly achieved while stirring on a hot plate at a temperature of about 45° C. Eighty-five (85) ml of butyl acetate was then added to the sodium hydroxide/methanol solution in aliquots while continuously stirring at 45° C. to keep the solution clear thereby forming a 15:85 (vol:vol) of methanol:butyl acetate mixture. The desired concentration of N-acetylcysteine and/or rifampin were then obtained by dissolving 5 mg of N-acetylcysteine and/or 4 mg of rifampin in the methanol:butyl acetate mixture to form the biofilm penetrating composition coating. The catheters were then dipped in the biofilm penetrating composition coating for 1 hour at 45° C., then removed from the biofilm penetrating composition coating and allowed to dry overnight. The catheters were gently rinsed with water and then allowed to dry for at least 4 before being gas sterilized with ethylene oxide.

The gas sterilized catheters were covered by a plastic sheath to ensure sterility of the surfaces and attached to the testing system. The bacterial suspension drained from the catheters into beakers during the 12 hour seeding phase as described above.

Growth phase: The lumens of the four catheters were infused with sterile TSB at a rate of 10 ml/hour for 24 hours to allow for biofilm formation. The infused TSB drained from the catheters into beakers.

The catheters were cultured using the sonication technique discussed above in Example 1. After 48 hours of incubation at 37° C., colony counts were obtained for each 3 cm piece of catheter and the mean number of colonies was calculated for each biofilm penetrating composition coating treatment. The results are in Table V.

TABLE V

| Catheter | Mean Number of Colonies (cfu per 3 cm segment) |
| --- | --- |
| 9 | 75 |
| 10 | 120 |
| 11 | 0 |
| 12 | 0 |

These results show that catheters coated with N-acetylcysteine and rifampin together completely prevent growth of *Staphylococcus epidermidis* on the surface of the catheter.

EXAMPLE 3

An in vitro model consisting of the modified Robbin's Device ("MRD") was used to study the formation of biofilm and colonization of catheter segments by *Staphylococcus epidermidis*. The MRD is described in greater detail in Nickel, et. al. "Tobramycin resistance of *Pseudomonas aeruginosa* cells growing as a biofilm on urinary catheter material," Antimicrobial Agents and Chemotherapy, 27:619–624 (1985) which is hereby incorporated by reference in its entirety.

The MRD is constructed of an acrylic block 42 cm long with a lumen of 2 mm×10 mm. The MRD has 25 evenly spaced specimen plugs, each connected to a 1 cm silicone catheter segment whose anterior surface (0.3 $cm^2$) comes in contact with the flushed infusate coming from a connected tubing and infusion bag.

Six different types of silicone catheter segments were coated as described in Example 3 above with the differences being in the concentrations of the biofilm penetrating agent and/or antimicrobial agent present in the biofilm penetrating composition coating. The six different catheters in Table VI were studied in triplicate.

TABLE VI

| Catheter | Catheter Coating Composition |
| --- | --- |
| 13 | Control uncoated catheter |
| 14 | Catheter coated with N-acetylcysteine (50 mg/ml of coating composition) |
| 15 | Catheter coated with minocycline (25 mg/ml of coating composition) |
| 16 | Catheter coated with N-acetylcysteine (50 mg/ml of coating composition) and minocycline (25 mg/ml of coating composition) |
| 17 | Catheter coated with chloroxylenol (50 mg/ml of coating composition) |
| 18 | Catheter coated with N-acetylcysteine (50 mg/ml of coating composition) and chloroxylenol (50 mg/ml of coating composition) |

The MRD was washed five times with 70% ethanol followed by five washings with distilled deionized water.

After placing the catheter segments in the MRD, the entire apparatus was gas sterilized by ethylene oxide.

Seeding phase: A bag that contained a bacterial suspension of *Staphylococcus epidermidis* $10^5$ cfu/ml of 5% dextrose in water) was connected to the MRD via an intravenous administration set and allowed to run for 2 hours at 60 ml/hour at room temperature. The effluent solution from the MRD was drained into beakers during the 2 hour seeding phase.

Growth phase: Sterile TSB was run into the MRD at 10 ml/hour for 48 hours. The effluent TSB from the MRD was drained into beakers during the 48 hour seeding phase.

Wash phase: Sterile saline solution was run through the MRD at 40 ml/hour for 4 hours. The effluent saline solution was drained into beakers during the 4 hour washing phase.

Catheter segments were cultured by placing each catheter segment in 5 ml phosphate buffered saline and sonicated for 10 minutes. One hundred microliter aliquots were plated onto chocolate agar plates for plat counts after incubation at 37° C. for 18 hours. The colony counts for each catheter segment for each biofilm penetrating composition coating in Table VI was counted and the mean for each biofilm penetrating composition coating was determined. Results are in Table VII.

TABLE VII

| Catheter | Mean Number of Colonies (cfu per 3 cm segment) |
| --- | --- |
| 13 | Too numerous to count |
| 14 | Too numerous to count |
| 15 | 25,200 |
| 16 | 12,000 |
| 17 | 14,750 |
| 18 | 3,650 |

These results show that catheter segments coated with a biofilm penetrating composition having a combination of N-acetylcysteine and either minocycline or chloroxylenol provides synergistic antimicrobial activity that substantially inhibits the growth and proliferation of *Staphylococcus epidermidis* on the surface of catheters coated with the biofilm penetrating composition.

It is to be understood that the invention is not limited to the exact details of construction, operation, exact materials, or embodiments shown and described, as obvious modifications and equivalents will be apparent to one skilled in the art. For example, the biofilm penetrating composition may be combined with antimicrobial agents or antimicrobial compositions e.g., rifamycins (e.g., rifampin), tetracyclines (e.g., minocycline), macrolides (e.g., erythromycin), peniclillins (e.g., nafcillin), cephalosporins (e.g., cefazolin), carbepenems (e.g., imipenem), monobactams (e.g., aztreonam), aminoglycosides (e.g., gentamicin), chloramphenicol, sulfonamides (e.g., sulfamethoxazole), glycopeptides (e.g., vanomycin), metronidazole, clindamycin, mupirocin, quinolones (e.g., ofloxacin), beta-lactam inhibitors (e.g., sulbactam and clavulanic acid), chloroxylenol, hexachlorophene, cationic biguanides (e.g., chlorhexidine and cyclohexidine), methylene chloride, iodine and iodophores (e.g., povidone-iodine), triclosan, furan medical preperations (e.g., nitrofurantoin and nitrofurazone), methenamine, aldehydes (e.g., glutaraldehyde and formaldehyde), alcohols, cetylpyridinium chloride, methylisothiazolone, thymol, a-terpineol, and any other antimicrobial agent or composition known to persons skilled in the art, to provide medical devices having biofilm penetrating capabilities and antimicrobial capabilities. Further, the biofilm penetrating composition may be combined with antifungal agents or antifungal compositions, including, but not limited to polyenes (e.g., amphotericin B), azoles (e.g., fluconazole), nystatin, amorolfine, ciclopirox, terbinafine, naftifine, and any other antifungal agent or composition known to persons skilled in the art, to provide medical devices having biofilm penetrating capabilities and antifungal capabilities. Also, the biofilm penetrating composition may be combined with microbial activity indicators which indicate the presence of microorganisms on the surface of the medical device. Accordingly, the invention is therefore to be limited only by the scope of the appended claims and equivalents thereof.

What is claimed is:

1. A method for substantially preventing the growth or proliferation of biofilm embedded microorganisms on at least one surface of a medical device comprising the steps of:

provided a medical device having at least one surface;

providing a biofilm penetrating composition having at least one biofilm penetrating agent; and contacting the biofilm penetrating composition to the medical device in an amount sufficient to substantially prevent the growth or proliferation of biofilm embedded microorganisms on the at least one surface of the medical device.

2. The method of claim 1, wherein the biofilm penetrating composition is formed by mixing cysteine or derivatives thereof and a base material.

3. The method of claim 1, wherein the biofilm penetrating composition is contacted to the medical device for a period of time sufficient to form a coating of the biofilm penetrating composition on the at least one surface of the medical device.

4. The method of claim 1, wherein the biofilm penetrating composition is contacted to the medical device by integrating the biofilm penetrating composition with the material forming the medical device during formation of the medical device.

5. The method of claim 1, wherein the biofilm penetrating composition is contacted to the medical device by flushing the medical device in the biofilm penetrating composition for a period of time sufficient to substantially prevent the growth or proliferation of biofilm embedded microorganisms on the at least one surface of the medical device.

6. A coated medic device having at least one surface which may substantially prevent the growth or proliferation of biofilm embedded microorganisms on the at least one surface of the coated medical device, comprising:

(a) a medical device; and (b) a biofilm penetrating composition coating having at least one biofilm penetrating agent for substantially preventing the growth or proliferation of biofilm embedded microorganisms on the at least one surface of the coated medical device, the biofilm penetrating composition coating being disposed upon the at least one surface.

7. The medical device of claim 6, wherein the biofilm penetrating composition coating further includes a base material.

8. The medical device of claim 6, wherein the at least one biofilm penetrating agent is selected from the group consisting of cysteine and derivatives thereof.

9. The medical device of claim 6, wherein the biofilm penetrating agent is selected from the group consisting of N-acetylcysteine and derivatives thereof.

10. The medical device of claim 7, wherein the base material is a buffer solution.

11. A method for removing substantially all biofilm embedded microorganisms from a medical device having at least one surface, the at least one surface of the medical device having biofilm embedded microorganisms attached thereto, comprising the steps of:

provided a medical device having at least one surface, the at least one surface of the medical device having biofilm embedded microorganisms attached thereto;

providing a biofilm penetrating composition, wherein the biofilm penetrating composition is formed by mixing at eat one biofilm penetrating agent and a base material; and contacting the biofilm penetrating composition with the medical device in an amount sufficient to remove substantially all of the biofilm embedded microorganisms from the at least one surface of the medical device.

12. The method of claim 11, wherein the biofilm penetrating agent is selected from the group consisting of cysteine and derivatives thereof.

13. The method of claim 11, wherein the biofilm penetrating agent is selected from the group consisting of N-acetylcysteine:and derivatives thereof.

14. The method of claim 13, wherein the base material is a buffer solution.

15. The method of claim 11, wherein the biofilm penetrating composition is contacted to the medical device by flushing the medical device in the biofilm penetrating composition for a period of time sufficient to remove substantially all biofilm embedded microorganisms on the at least one surface of the medical device.

* * * * *